United States Patent [19]

Hilscher et al.

[11] Patent Number: 4,853,390

[45] Date of Patent: Aug. 1, 1989

[54] (2-HALOERGOLINYL)-N'-N'-DIETHYLUREA COMPOUNDS USEFUL AS MEDICINAL AGENTS E.G., AS NEUROLEPTICS

[75] Inventors: Jean-Claude Hilscher; Wolfgang Kehr; Gerhard Sauer; Herbert Schneider; Helmut Wachtel, all of Berlin, Fed. Rep. of Germany

[73] Assignee: Schering Aktiengesellschaft, Berlin and Bergkamen, Fed. Rep. of Germany

[21] Appl. No.: 21,582

[22] Filed: Mar. 2, 1987

Related U.S. Application Data

[63] Continuation of Ser. No. 731,245, May 7, 1985, abandoned, which is a continuation-in-part of Ser. No. 559,068, Dec. 7, 1983, abandoned, which is a continuation of Ser. No. 339,566, Jan. 15, 1982, abandoned.

[30] Foreign Application Priority Data

Jan. 14, 1981 [DE] Fed. Rep. of Germany ....... 3101535

[51] Int. Cl.[4] ..................... A61K 31/48; C07D 457/12
[52] U.S. Cl. ....................................... 514/288; 546/68
[58] Field of Search ........................... 546/68; 514/288

[56] References Cited

U.S. PATENT DOCUMENTS

| 4,348,391 | 7/1982 | Stutz et al. | 546/68 |
| 4,348,392 | 9/1982 | Fehr et al. | 546/68 |
| 4,379,790 | 4/1983 | Horowski et al. | 546/68 |
| 4,417,051 | 11/1983 | Sauer | 546/68 |

FOREIGN PATENT DOCUMENTS

| 56358 | 7/1982 | European Pat. Off. | 546/68 |
| 118848 | 9/1984 | European Pat. Off. | 546/68 |
| 141387 | 5/1985 | European Pat. Off. | 546/68 |
| 2530577 | 1/1976 | Fed. Rep. of Germany . | |
| 2924102 | 12/1980 | Fed. Rep. of Germany | 546/68 |
| 615929 | 3/1980 | Switzerland | 546/68 |

1567484 5/1980 United Kingdom .

OTHER PUBLICATIONS

Krepelka et al., "Some N-(D-6-Methyl-8-Ergolin-l-yl Methyl)-N-Substituted Areas . . .," *Collection of Czecholov. Chem. Commun.*, vol. 42, pp. 1417-20 (1977).

Primary Examiner—Donald G. Daus
Assistant Examiner—Cecilia Shen
Attorney, Agent, or Firm—Millen & White

[57] ABSTRACT (2-Haloergolinyl)-N',N'-diethylurea derivatives of Formula I

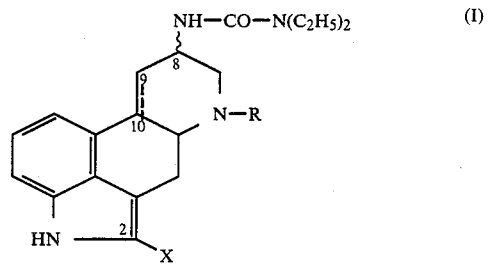

and the salts thereof, wherein
R is hydrogen, alkyl of up to 6 carbon atoms, or alkenyl of up to 3 carbon atoms,
X is halogen,

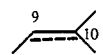

is a CC single or CC double bond, and the urea residue in the 8-position can be in the α- or β-configuration, have neuropsychotropic properties.

As a result, they are excellently suitable for treatment of psychotic disturbances and emesis.

23 Claims, No Drawings

(2-HALOERGOLINYL)-N'-N'-DIETHYLUREA COMPOUNDS USEFUL AS MEDICINAL AGENTS E.G., AS NEUROLEPTICS

CROSS-REFERENCE TO RELATED APPLICATIONS

This application is a continuation of application Ser. No. 731,245 filed May 7, 1985, now abandoned, which is a continuation-in-part of Ser. No. 559,068, filed Dec. 7, 1983, now abandoned, which is a continuation of Ser. No. 339,566, filed Jan. 15, 1982, now abandoned.

The present invention concerns novel (2-haloergolinyl)-N',N'-diethylurea derivatives, their preparation and use.

SUMMARY OF THE INVENTION

It is an object of this invention to provide new compounds having valuable pharmacological properties.

Upon further study of the specification and appended claims, further objects and advantages of this invention will become apparent to those skilled in the art.

The objects have been achieved by providing (2-haloergolinyl)-N',N'-diethylurea derivatives of Formula I

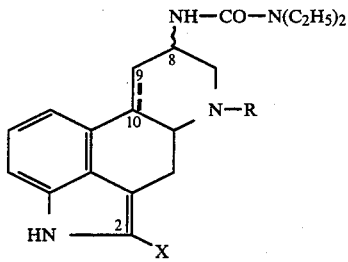

and the salts thereof,
wherein
R is hydrogen, alkyl of up to 6 carbon atoms, or alkenyl of up to 3 carbon atoms,
X is a halogen atom, preferably chlorine or bromine, but also iodine, most preferably bromo.

is a CC single or CC double bond, and the 8-positioned urea residue can be in the α- or β-position, with the proviso that when the 8-urea group is in the α-configuration, R is CH$_3$, and 9═══10 is a single bond, then X is not chloro.

DETAILED DISCUSSION

The salts of the compounds of this invention are acid addition salts and are derived from acids which produce physiologically acceptable salts. Such acids include inorganic acids, such as, for example, hydrochloric acid, nitric acid, phosphoric acid, sulfuric acid, hydrobromic acid, hydriodic acid, nitrous acid, or phosphorous acid; and organic acids, such as, for example, aliphatic mono- or dicarboxylic acids, phenylsubstituted alkanecarboxylic acids, hydroxyalkanecarboxylic acids, or alkanedicarboxylic acids; aromatic acids or aliphatic or aromatic sulfonic acids. Physiologically acceptable salts of these acids include, therefore, e.g. the corresponding sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, mandelate, butyne-1,4-dioate, hexyne-1,6-dioate, benzoate, chlorobenzoate, methylebenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, maleate, tartrate, methanesulfonate, propanesulfonate, naphthalene-1-sulfonate, naphthalene-2-sulfonate, orotate and the like.

The alkyl residues of up to 6 carbon atoms include those derived from aliphatic and cycloaliphatic hydrocarbons, such as, for example, ethyl, n-propyl, isopropyl, n-butyl, isobutyl, tert-butyl, n-pentyl, cyclopropylmethyl, cyclobutylethyl, cyclopentylmethyl, cyclobutyl, cyclopropyl, cyclopentyl, etc.

Alkenyl of up to 3 carbon atoms includes, in particular, allyl; and also vinyl or 2-methylvinyl.

The present invention furthermore concerns a process for preparing the compounds of this invention comprising conventionally halogenating (ergolinyl)-N',N'-diethyl-urea compounds in the 2-position or halogenating lysergic acid methyl ester derivatives in the 2-position, and subsequently introducing the N',N'-diethylurea group.

More particularly, the invention concerns a process for preparing (2-haloergolinyl)-N',N'-diethylurea derivatives of Formula I

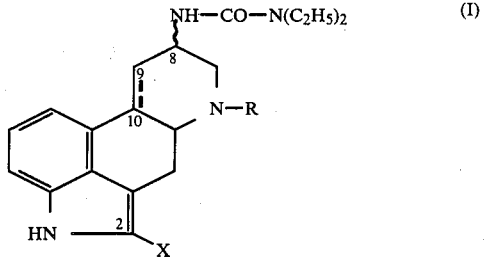

and the salts thereof,
wherein
R is hydrogen, alkyl of up to 6 carbon atoms, or alkenyl of up to 3 carbon atoms,
X is a halogen atom, preferably chlorine or bromine,

is a CC single or CC double bond, and the 8-positioned urea residue can be in the α- or β-configuration, comprising, in conventional manner, either (a) directly halogenating the corresponding (ergolinyl)-N',N'-diethylurea derivatives of Formula II

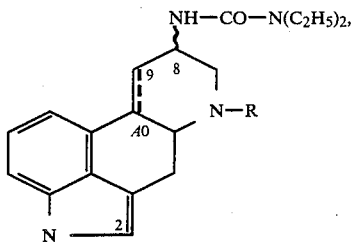

wherein R is as defined above, or (b) halogenating lysergic acid methyl ester derivatives of Formula III

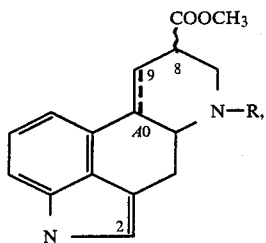

wherein R is as defined above;

reacting the resultant 2-halolysergic acid methyl ester with hydrazine to the hydrazide; converting the latter into the azide with nitrous acid; forming the isocyanate by heating; then reacting the latter with diethylamine;

and, optionally, converting the resultant compounds into the salts thereof.

Consequently, the halogenation reaction can be accomplished in two ways:

(a) directly at the 2-position of the (ergolinyl)-N',N'-diethylurea compound; or (b) lysergic acid methyl ester derivatives can be halogenated in the 2-position; the hydrazide formed with hydrazine; the hydrazide converted into the azide with nitrous acid; the product heated with formation of the isocyanate, and this reacted with diethylamine;

if desired, the resultant compound can be converted into its salt.

To conduct the process of this invention, the (ergolinyl)-N',N'-diethylurea compounds or the lysergic acid methyl ester derivatives are halogenated with a halogenating agent preferably at room temperature in an inert solvent. In this process, the (2-haloergolinyl)-N',N'-diethylurea compounds are, in part, obtained directly as the hydrogen halogenides. To control the reaction, it is suitable to operate with the exclusion of air and light.

Suitable chlorinating agents include N,2,6-trichloro-4-nitroacetanilide, N'-chlorosuccinimide, N-chlorosaccharin, tert-butyl hypochlorite, N-chloroacetanilide, N-chlorophthalimide, N-chlorotetrachlorophthalimide, 1-chlorobenzotriazole, N-chloro-2,4,6-trichloroacetanilide, thionyl chloride, sulfuryl chloride, sulfuryl chlorofluoride, cyanuric trichloride, copper (II) chloride, hexachloroacetone, tetraalkylammonium perchloride, such as tetramethylammonium perchloride and sodium hypochlorite.

Suitable for the introduction of bromine are N-bromosuccinimide, as well as N-bromoacetamide, N-bromophthalimide, N,N-dibromohydantoin, N-bromo-p-toluenesulfamide, N-bromo-di-p-toluenesulfimide, pyrrolidone-(2)-hydrotribromide, N-bromocaprolactam, dioxane dibromide, pyridinium bromide, pyridinium perbromide, phenyltrimethylammonium bromide, phenyltrimethylammonium perbromide, 3-bromo-6-chloro-2-methylimidazo[1,2-b]pyridazine as the bromine complex, copper (II) bromide, sodium hypobromite, 5,5-dibromo-2,2-dimethyl-4,6-dioxo-1,3-dioxane, 2,4,4,6-tetrabromocyclohexa-2,5-dienone, 2-carboxyethyltriphenylphosphonium perbromide, tetraalkylammonium perbromide, such as tetramethylammonium perbromide, and 1,3-dibromo-5,5-dimethylhydantoin.

N-Iodosuccinimide is especially preferred as the iodination agent.

These halogenating agents can be utilized in various solvents with or without radical initiators.

Suitable solvents include in all cases those which are inert with respect to the reactants. Examples include aliphatic and cyclic ethers, such as diethyl ether, methylethyl ether, tetrahydrofuran, and dioxane; halogenated hydrocarbons, such as methylene chloride, chloroform, and carbon tetrachloride; polar aprotic solvents, such as hexamethylphosphoric triamide, acetonitrile, dimethylformamide, N-methylpyrrolidone, dimethylacetamide, and tetramethylurea; saturated and unsaturated carbocyclics, such as hexane, benzene, and toluene; as well as ketones, such as acetone, cyclohexanone, methyl ethyl ketone, and methyl isobutyl ketone.

The solvents can be used individually or in admixture with one another.

To effect the halogenation reaction, it may be advantageous to add a catalyst ("radical starter") to the reaction mixture. Suitable, for example, are Lewis acids, e.g., aluminum trichloride and boron trifluoride etherate, or azo compounds, such as 2,2-azobis(2-methylpropionitrile).

After the halogenation of process version (b), the 2-halolysergic acid ester derivative is reacted in a second stage with anhydrous hydrazine to form the corresponding hydrazides, but with omission of isomer separation.

In the third stage, the resultant hydrazide is converted into the acid azide with nitrous acid, and the aqueous reaction mixture is combined with a buffer, such as sodium bicarbonate, disodium hydrogen phosphate, sodium acetate, potassium borate, or ammonia, and extracted with toluene.

In the fourth stage, the toluene phase is heated to temperatures above room temperature, preferably 70° C. to the boiling temperature of the reaction mixture, thus forming the corresponding isocyanate.

In the fifth stage, the thus-formed isocyanate is made to react with diethylamine at room temperature, resulting in an isomeric mixture of 2-halogenated N',N-diethylurea derivatives which are suitably separated by chromatography.

The starting compounds for the process of this invention can be prepared, where they are unknown, analogously to conventional methods. (See, e.g., T. Fehr et al, Helv. Chim. Acta 53 : 2197 [1970]; J. Krepelka et al, Coll. Czech. Chem. Commun. 42 : 1209 [1977]; and U.S. Pat. application Ser. No. 159,280, filed on June 13, 1980, whose disclosure is incorporated by reference herein.)

If the desired compounds are saturated in the 9,10-position, then the starting compounds are suitably hydrogenated in a conventional fashion before halogenation. Suitable methods include hydrogenation with hydrogen in the presence of palladium on carbon or other suitable supports, such as lime, in the presence of platinum, e.g., in the form of platinum black, or in the presence of nickel, e.g., in the form of Raney nickel. The product is subsequently purified by chromatography and/or separated into the isomers.

The 2-halogenated N',N'-diethylurea compounds of this invention can be purified by recrystallization and/or chromatograpy, either as the free bases or in the form of their acid addition salts. The latter are obtained, if desired, by reaction with a physiologically compatible acid, e.g., tartaric acid, maleic acid, or benzoic acid under fully conventional procedures.

The compounds of this invention effect a pronounced blockage of dopaminergic and noradrenergic receptors and differ surprising in their quality of efficacy from the conventional lisuride hydrogen maleate and other non-2-halogenated analogs. As a result of this activity, the compounds of this invention are valuable neuroleptics, i.e., antipsychotic agents.

Supplementarily, the compounds of this invention show in mice and rats a neuroleptic-like spectrum of activity manifesting itself, inter alia, by the occurrence of catalepsy, ptosis, and hypothermia. (These symptoms according to Papeschi are reliable indicators for neuroleptic effects, see Papeschi, R. : Dopamine Extrapyramidal System and Psychomotor Function; Psychiat. Neurol. Neurochirurg. 75: 13–48, 1972.)

Moreover, the compounds of this invention also have a circulation-promoting effect.

On the basis of these pharmacological properties, the compounds of this invention are suitable, for example, for treatment of psychotic disturbances and emesis.

To use the compounds of this invention as medicinal agents, for such purposes, e.g., for administration to mammals, including humans, they can be brought into the shape of a pharmaceutical preparation containing, in addition to the active compound, pharmaceutically acceptable, organic or inorganic, inert vehicles suitable for enteral or parenteral administration, such as, for example, water, gelatin, gum arabic, lactose, amylose, magnesium stearate, talc, vegetable oils, polyalkylene glycols, etc. The pharmaceutical preparations can be made in the solid form, e.g., as tablets, dragees, suppositories, capsules, or in the liquid form, e.g., as solutions, suspensions, or emulsions. Optionally they can contain, additionally, compatible auxiliary agents, such as preservatives, stabilizers, wetting agents, or emulsifiers, salts to vary the osmotic pressure, or buffers.

For parenteral application, particularly suitable are injectable sterile solutions, preferably aqueous solutions, as well as suspensions or emulsions. Ampoules are convenient unit dosages.

For enteral application, particularly suitable are tablets, dragees or capsules having talc and/or a carbohydrate carrier or binder or the like, the carrier preferably being lactose and/or cornstarch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 0.05 –2 mg. in a pharmaceutically acceptable carrier per unit dosage.

The dosage of the compounds according to this invention is 0.1 –1.0 mg/day when administered to patients, e.g., humans, e.g., for the treatment of psychotic disturbances, e.g., schizophrenia. 2-Bromolisuride (3-(9,10-didehydro-6-methyl-2-bromo-8α-ergolinyl)-1,1-diethylurea) is a preferred agent of this invention. Administration of the compounds of this invention can be effected analogously to that of the known agent, e.g., haloperidol.

Without further elaboration, it is believed that one skilled in the art can, using the preceding description, utilize the present inventin to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

250 mg of 1,1-diethyl-3-(9,10-didehydro-6-methyl-8α-ergolinyl)urea was stirred in 225 ml of dioxane with 250 mg of N-chlorosuccinimide for 70 hours under exclusion of light and with nitrogen purging at 90° C.; the reaction mixture was then cooled to room temperature, poured into 300 ml of water, extracted with methylene chloride, dried over sodium sulfate, and concentrated to an oil under vacuum.

After chromatographing over 100 times the quantity of silica gel with methylene chloride/acetone (95/5), the yield was 94 mg of 1,1-diethyl-3-(2-chloro-9,10-didehydro-6-methyl-8α-ergolinyl)urea, mp 105°–110° C.

$[\alpha] + 312°$ (chloroform)

EXAMPLE 2

1,42 g of 1,1-diethyl-3-(9,10-didehydro-6-methyl-8α-ergolinyl)urea was agitated in 142 ml of dioxane with 1.42 g of N-bromosuccinimide for 30 minutes under exclusion of light and with nitrogen purging at room temperature; the reaction mixture was then filtered. The residue was washed with 50 ml of dioxane. The combined filtrates were concentrated to an oil under vacuum, combined with 30 ml of ethyl acetate, heated, then cooled to room temperature, the resultant crystals were vacuum-filtered and heated with 30 ml of diethyl ether, again cooled to room temperature, and this procedure was repeated with 30 ml of isopropyl ether. Yield: 530 mg of 1,1-diethyl-3-(2-bromo-9,10-didehydro-6-methyl-8α-ergolinyl)urea as the hydrogen bromide salt, mp 209°–210° C.

UV: $\epsilon_{225} = 21,300$; $\epsilon_{242} = 22,400$; $\epsilon_{303} = 9,600$; $(\epsilon_{321} = 8,530)$

EXAMPLE 3

10.0 g of 1,1-diethyl-3-(9,10-didehydro-6-methyl-8β-ergolinyl)urea was stirred in 1,000 ml of dioxane with 10.0 g of N-bromosuccinimide for 30 minutes under exclusion of light and with nitrogen purging at room temperature and then filtered. The residue was washed with 300 ml of dioxane. The combined filtrates were concentrated to an oil under vacuum, then dissolved in 30 ml of methanol. The solution was subsequently poured into 1,000 ml of diethyl ether. The crystals produced in this way were removed by means of vacuum-filtration, thus obtaining 3.79 g of 1,1-diethyl-3-(2-bromo-9,10-didehydro-6l-methyl-8β-ergolinyl)urea as the hydrogen bromide salt, mp 189°–193° C.

$[\alpha]_D + 44.4°$ (in methanol)

UV: $\epsilon_{223} = 23,200$; $\epsilon_{238} = 23,000$; $\epsilon_{300} = 10,900$

EXAMPLE 4

(a) 5.35 g of lysergic acid methyl ester was dissolved in 72 ml of tetrahydrofuran and 8 ml of hexamethylphosphoric triamide. A solution of 10.70 g of phenyltrimethylammonium perbromide in 267 ml of tetrahydrofuran was added dropwise to this mixture at room temperature under nitrogen purging. After stirring for 2 hours at room temperature, the mixture was vacuum-filtered, the residue was washed with 80 ml of tetrahydrofuran and recrystallized from methanol in the presence of active carbon. Yield 4.50 g of 2-bromolysergic acid methyl ester as the hydrobromide, mp 124°–125° C.

(b) 4.24 g of the methyl ester of 2-bromolysergic acid hydrobromide was dissolved in 254 ml of chloroform and stirred with 106 ml of anhydrous hydrazine for 17 hours under nitrogen purging at 50° C. The mixture was then cooled to room temperature and extracted with 500 ml of a saturated sodium chloride solution. The phases were separated. The aqueous phase was extracted three thimes with chloroform. The combined chloroform phases were washed twice with water and dried over sodium sulfate. Evaporation under vacuum and crystallization from 25 ml of methanol yielded 2.35 g of isomeric 2-bromo(iso)lysergic acid hydrazide, mp 218° C. (decomposition).

$[\alpha] +343.2°$ (in pyridine)

(c) 1.0 g of isomeric 2-bromo(iso)lysergic acid hydrazide was dissolved in 18 ml of 0.2N hydrochloric acid and combined under ice cooling with 3.5 ml of 1N sodium nitrite solution and 21.5 ml of 0.2N hydrochloric acid. After about 5 minutes, the mixture was distributed between 170 ml of toluene and 28.5 ml of 1N ammonium hydroxide solution; the phases were separated and the aqueous phase was extracted with additional toluene, dried over sodium sulfate, the toluene phase heated to 90° C. for 15 minutes under nitrogen purging and then cooled to room temperature. The toluene solution was combined with 2.5 ml of freshly distilled diethylamine and stirred for one hour under nitrogen purging. After concentration under vacuum an oil (1.0 g) was obtained yielding 1,1-diethyl-3-(2-bromo-9,10-didehydro-6-methyl-8β-ergolinyl)urea, mp 204°–208° C. by preparative thin-layer chromatography.

EXAMPLE 5

0.80 g of 1,1-diethyl-3-(6-methyl-8α-ergolinyl)urea was stirred in 80 ml of dioxane with 0.80 g of N-bromosuccinimide for 3.5 hours under exclusion of light and with nitrogen purging and then filtered. The residue was washed twice with respectively 50 ml of dioxane. The combined filtrates were concentrated to an oil under vacuum, made to crystallize with 20 ml of ethyl acetate, and the thusisolated crystals were washed twice with respectively 5 ml of ethyl acetate and dried.

The crude product was first recrystallized from an ethyl acetate-methanol mixture (95/5) and active carbon and then in methanol and precipitated in ether, thus obtaining 370 mg of 1,1-diethyl-3-(2-bromo-6-methyl-8α-ergolinyl)-urea as the hydrogen bromide salt, mp 226°–228° C. (decomposition).

$[\alpha]_D +62.9°$ (in pyridine; c=0.5)

EXAMPLE 6

1.0 g of 1,1-diethyl-3-(6-methyl-8β-ergolinyl)-urea was dissolved in 15 ml of tetrahydrofuran containing 10% hexamethylphosphoric triamide. Then 2.0 g of phenyltrimethylammonium perbromide was added dropwise thereto at room temperature within 10 minutes, and the reaction mixture was agitated at room temperature for 6 hours in a nitrogen atmosphere under exclusion of light and then filtered. The residue (1.37 g) was washed with 20 ml of tetrahydrofuran. The tetrahydrofuran filtrates were poured into 500 ml of ether, the resultant crystalline precipitate was isolated and chromatographed together with the thus-obtained residue in chloroform over neutral aluminum oxide. Yield: 650 mg of 1,1-diethyl-3-(2-bromo-6-methyl-8β-ergolinyl)urea, mp 194°–195° C.

$[\alpha]_D -71.2°$ (in pyridine)

To form the hydrogen bromide salt, 240 mg of 1,1-diethyl-3-(2-bromo-6-methyl-8β-ergolinyl)urea was dissolved in 3 ml of acetone and precipitated into 100 ml of ether wherein 70 mg of gaseous hydrogen bromide was dissolved. The crystalline precipitate was filtered and washed first with 20 ml of ether and then with 3 ml of acetone, yielding 240 mg of hydrogen bromide salt, mp 212° C.

EXAMPLE 7

676 mg of 3-(9,10-didehydro-6-methyl-8β-ergolinyl)-1,1-diethylurea (2 millimoles) was dissolved in 38 ml of anhydrous acetonitrile. Under an inert as atmosphere and under cooling to −5° C., a solution of 0.6 ml of boron trifluoride etherate in 10 ml of anhydrous methylene chloride was added to the reaction mixture. Thereafter, under the same conditions, a solution of 0.18 ml of freshly distilled sulfuryl chloride in 20 ml of anhydrous methylene chloride was added dropwise with 10 minutes. After 30 minutes, this solution was introduced into a cooled, aqueous 5% ammonia solution, extracted with methylene chloride, the organic phase dried with magnesium sulfate, and evaporated. From the crude product, 420 mg of 3-(2-chloro-9,10-didehydro-6-methyl-8β-ergolinyl)-1,1-diethylurea was separated by chromatography.

$[\alpha]_D +51°$ (chloroform)

EXAMPLE 8

In the same was as described in Example 7, 340 mg of 1,1-diethyl-3(6-methylergolinyl)urea (1 millimole) was dissolved in 19 ml of anhydrous acetonitrile and 0.3 ml of boron trifluoride etherate in 5 ml of anhydrous methylene chloride and reacted with 0.09 ml of freshly distilled sulfuryl chloride, dissolved in 10 ml of anhydrous methylene chloride. The product was worked up and chromatographed as described in Example 7, thus obtaining 270 mg of 3-(2-chloro-6-methyl-8β-ergolinyl)-1,1-diethylurea.

$[\alpha]_D -60°$ (chloroform)

EXAMPLE 9

Analogously to Example 7, 1 mmol of 1,1-diethyl-3-(9,10-didehydro-8β-ergolinyl)urea resulted in a 40% yield of 1,1-diethyl-3-(2-chloro-9,10-didehydro-8α-ergolinyl)urea.

$[\alpha]_D +326°$ (chloroform)

In the same way, the corresponding following 2-halogen compounds were prepare from 1 mmol of starting material of Formula II:

| Compound | Yield [%] | $[\alpha]_D°$ |
| --- | --- | --- |
| 1,1-Diethyl-3-(2-chloro-8α-ergolinyl)urea | 71 | +49 |

-continued

| Compound | Yield [%] | $[\alpha]_D°$ |
|---|---|---|
| 1,1-Diethyl-3-(2-chloro-6-ethyl-8α-ergolinyl)urea | 93 | +5 |
| 1,1-Diethyl-3-(2-chloro-6-ethyl-9,10-didehydro-8α-ergolinyl)urea | 98 | +196 |
| 1,1-Diethyl-3-(2-chloro-6-n-propyl-8α-ergolinyl)urea | 90 | +13 |
| 1,1-Diethyl-3-(2-chloro-6-n-propyl-9,10-didehydro-8α-ergolinyl)urea | 92 | |
| 1,1-Diethyl-3-[2-chloro-6-(2-propenyl)-8α-ergolinyl]-urea | 26 | −2 |
| 1,1-Diethyl-3-[2-chloro-6-(2-propenyl)-9,10-didehydro-8α-ergolinyl]urea | 21 | |

EXAMPLE 10

1 mmol of starting material of Formula II was dissolved in 150 ml of anhydrous dioxane, cooled in an ice bath, combined with 650 mg of pyrrolidinone hydrogen perbromide (2 mmol), and agitated at room temperature or with external ice cooling. The progress of the reaction was controlled by chromatography and, if necessary, additional brominating agent was introduced. Subsequently, 50 ml of acetone and then concentrated ammonia solution were added until an alkaline reaction was obtained. The mixture was extracted with methylene chloride, the organic phase was dried with magnesium sulfate and chromatographed on silica gel.

The following compounds were produced in this way:

| Compound | Yield [%] | $[\alpha]_D°$ |
|---|---|---|
| 1,1-Diethyl-3-(2-bromo-8α-ergolinyl)urea | 89 | +47 |
| 1,1-Diethyl-3-(2-bromo-9,10-didehydro-8α-ergolinyl)urea | 79 | +263 |
| 1,1-Diethyl-3-(2-bromo-6-methyl-8α-ergolinyl)urea | 92 | |
| 1,1-Diethyl-3-(2-bromo-6-ethyl-8α-ergolinyl)urea | 84 | +3 |
| 1,1-Diethyl-3-(2-bromo-6-ethyl-9,10-didehydro-8α-ergolinyl)urea | 73 | |
| 1,1-Diethyl-3-(2-bromo-6-n-propyl-8α-ergolinyl)urea | 75 | +1 |
| 1,1-Diethyl-3-(2-bromo-6-n-propyl-9,10-didehydro-8α-ergolinyl)urea | 80 | |
| 1,1-Diethyl-3-[2-bromo-6-(2-propenyl)-8α-ergolinyl]urea | 17 | 0 |
| 1,1-Diethyl-3-[2-bromo-6-(2-propenyl)-9,10-didehydro-8α-ergolinyl]urea | 12 | |

EXAMPLE 11

1 mmol of starting material was dissolved in 20 ml of anhydrous dioxane, combined at room temperature with about 1,5 ml of N-iodosuccinimide, and agitated for 30 minutes. The reaction mixture was then poured into a saturated bicarbonate solution, extracted with methylene chloride, and the organic phase was dried with magnesium sulfate. After evaporation of the solvent, the residue was chromatographed on silica gel.

With this method, the following compounds were produced:

| Compound | Yield [%] | $[\alpha]_D°$ |
|---|---|---|
| 1,1-Diethyl-3-(2-iodo-6-methyl-8α-ergolinyl)urea | 76 | +8 |
| 1,1-Diethyl-3-(2-iodo-6-methyl-9,10-didehydro-8α-ergolinyl)urea | 23 | +168 |

EXAMPLE 12

0.5 mmol of 2-haloergoline derivative is dissolved in 1 ml of methylene chloride, and a solution of 0.25 mmol of tartaric acid in 1 ml of methanol is added thereto. The tartrate is separated, in some cases only after adding a small amount of diisopropyl ether.

The following tartrates were produced by this method:

| Compound | Yield [%] | $[c]_D°$ |
|---|---|---|
| 1,1-Diethyl-3-(2-chloro-6-methyl-8α-ergolinyl)urea tartrate | 74 | +27 |
| 1,1-Diethyl-3-(2-chloro-6-methyl-8β-ergolinyl)urea tartrate | 65 | −54 |
| 1,1-Diethyl-3-(2-chloro-6-methyl-9,10-didehydro-8α-ergolinyl)urea tartrate | 50 | +245 |
| 1,1-Diethyl-3-(2-chloro-6-methyl-9,10-didehydro-8β-ergolinyl)urea tartrate | 45 | +92 |
| 1,1-Diethyl-3-(2-iodo-6-methyl-8α-ergolinyl)urea tartrate | 78 | +34 |
| 1,1-Diethyl-3-(2-iodo-6-methyl-9,10-didehydro-8α-ergolinyl)urea tartrate | 71 | +124 |
| 1,1-Diethyl-3-(2-bromo-6-n-propyl-8α-ergolinyl)urea hydrogen tartrate | 65 | +18 |
| 1,1-Diethyl-3-(2-bromo-6-n-propyl-9,10-didehydro-8α-ergolinyl)urea tartrate | 66 | +165 |
| 1,1-Diethyl-3-[2-chloro-6-(2-propenyl)-8α-ergolinyl]-urea tartrate | 65 | +13 |
| 1,1-Diethyl-3-[2-chloro-6-(2-propenyl)-9,10-didehydro-8α-ergolinyl]urea hydrogen tartrate | 49 | +182 |
| 1,1-Diethyl-3-[2-bromo-6-(2-propenyl)-8α-ergolinyl]-urea tartrate | 60 | +12 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A (2-Haloergolinyl)-N',N'-diethylurea of the formula

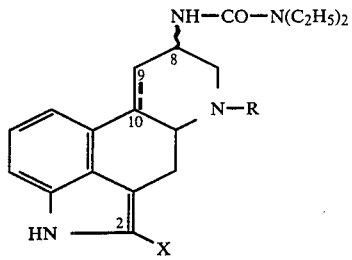

or a pharmaceutically acceptable salt thereof,
wherein
R is hydrogen or alkyl of up to 6 carbon atoms,
X is halogen,

is a CC single or CC double bond, and the 8-positioned urea residue is in the α— or β— configuration,
with the proviso that when, R is CH₃, and 9 ‒ ‒ ‒ 10 is a single bond, then X is not chloro.

2. A compound of claim 1 wherein X is chloro, bromo or iodo.

3. A compound of claim 1 wherein R is alkyl.

4. 1,1-Diethyl-3-(2-chloro-9,10-didehydro-6-methyl-8α-ergolinyl)urea or the hydrogen chloride thereof, compounds of claim 1.

5. 1,1-Diethyl-3-(2-bromo-9,10-didehydro-6-methyl-8α-ergolinyl)urea or the hydrogen bromide thereof, compounds of claim 1.

6. 1,1-Diethyl-3-(2-bromo-9,10-didehydro-6-methyl-8β-ergoliny)urea or the hydrogen bromide thereof, compounds of claim 1.

7. 1,1-Diethyl-3-(2-bromo-6-methyl-8α-ergolinyl)-urea or the hydrogen bromide thereof, compounds of claim 1.

8. 1,1-Diethyl-3-(2-bromo-6-methyl-8β-ergolinyl)-urea or the hydrogen bromide thereof, compounds of claim 1.

9. 1,1-Diethyl-3-(2-chloro-9,10-didehydro-6-methyl-8β-ergolinyl)urea or the hydrogen chloride thereof, compounds of claim 1.

10. A neuroleptically useful pharmaceutical composition comprising an amount of a compound of claim 1 effective as a neuroleptic and a pharmaceutically acceptable carrier.

11. A pharmaceutical composition of claim 10 wherein the amount of active agent is 0.05–2 mg.

12. A method of acheiving a neuroleptic effect in a patient comprising administering to a patient in need of such treatment an amount of a compound of claim 1 effective as a neuroleptic.

13. A compound of claim 1 wherein X is bromo.

14. A compound of claim 1 wherein X is chloro.

15. A compound of claim 1 wherein

is a single bond.

16. A compound of claim 1 wherein

is a double bond.

17. A compound of claim 15 wherein X is Br or I.

18. A method of claim 12 wherein the patient is suffering from schizophrenia.

19. A compound of claim 1 wherein R is methyl.

20. A compound of claim 1 wherein the 8-positioned urea residue is in the 6ο-configuration.

21. A method of treating emesis in a patient comprising administering to the patient an effective amount of a compound of claim 1.

22. A method of achieving a neuroleptic effect in a patient comprising administering to a patient in need of such treatment an amount of a compound of claim 5 effective as a neuroleptic.

23. A neuroleptically useful pharmaceutical composition comprising an amount of a compound of claim 5 effective as a neuroleptic and a pharmaceutically acceptable carrier.

* * * * *